United States Patent [19]

Sung et al.

[11] 4,263,015

[45] Apr. 21, 1981

[54] RUST INHIBITOR AND OIL COMPOSITION CONTAINING SAME

[75] Inventors: Rodney L. Sung, Fishkill; Jerzy J. Bialy; Peter Dorn, both of Lagrangeville; William P. Cullen, Fishkill, all of N.Y.; John W. Nebzydoski, Miami, Fla.

[73] Assignee: Texaco Inc., White Plains, N.Y.

[21] Appl. No.: 940,928

[22] Filed: Sep. 11, 1978

Related U.S. Application Data

[63] Continuation of Ser. No. 753,962, Dec. 23, 1976, abandoned.

[51] Int. Cl.$^3$ .................... C10L 1/22; C07D 249/14
[52] U.S. Cl. .................... 44/63; 252/51.5 A; 252/392; 548/269

[58] Field of Search .............. 44/63; 252/51.5 A, 392; 260/308 R

[56] References Cited

U.S. PATENT DOCUMENTS

| | | | |
|---|---|---|---|
| 3,219,666 | 11/1965 | Norman et al. | 252/51.5 A |
| 3,272,746 | 9/1966 | Le Suer et al. | 252/51.5 A |

Primary Examiner—Winston A. Douglas
Assistant Examiner—Y. Harris-Smith
Attorney, Agent, or Firm—Carl G. Ries; Robert A. Kulason; James J. O'Loughlin

[57] ABSTRACT

A rust inhibitor comprising the reaction product of a hydrocarbylsuccinic anhydride in which the hydrocarbyl radical has from about 6 to 30 carbon atoms and an aminotriazole is provided. The rust inhibitor is effective in motor fuel and lubricating oil compositions.

15 Claims, No Drawings

RUST INHIBITOR AND OIL COMPOSITION CONTAINING SAME

This is a continuation of application Ser. No. 753,962 filed on Dec. 23, 1976 now abandoned.

BACKGROUND OF THE INVENTION

1. Field of the Invention

Motor fuel compositions obtained from the refining of petroleum are often manufactured at great distances away from the ultimate consumer. As a result, the fuel composition is transported over long distances via pipelines, ships or barges. The fuel is then usually trans-shipped via tank trucks and then stored for varying intervals of time at fuel depots or in service station storage tanks. During the various stages of transport and storage, the fuel composition is in contact with atmospheric moisture as well as coming in contact with water in tank bottoms. Fuel oil and lubricating oil compositions encounter many of the same conditions. The environment consisting of the ever present water and steel vessels used in transport or storage is highly susceptible to corrosion. It is essential for the maintenance of product standards and satisfactory product performance that metal corrosion, particularly ferrous metal corrosion, be prevented or minimized throughout the product distribution system for fuels and lubricants.

2. Summary of the Invention

The additive of the invention, which is effective as a rust inhibitor for motor fuels, fuel oils and lubricating oils, comprises the reaction product a hydrocarbyl-substituted anhydride and an aminotriazole.

SPECIFIC EMBODIMENTS OF THE INVENTION

The additive of the invention is obtained by reacting a hydrocarbyl-substituted succinic anhydride with an aminotriazole at a temperature ranging from about room temperature to about 150° C. until the substantial completion of the reaction. This reaction is conducted in the absence of any catalyst but generally in the presence of a solvent to facilitate the reaction.

The hydrocarbyl-substituted succinic anhydride reactant is represented by the formula:

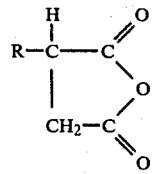

in which R is a monovalent aliphatic hydrocarbon radical having from about 6 to 30 carbon atoms. The hydrocarbon radical can be straight or branched chain hydrocarbon radical and can be saturated or unsaturated. Particularly preferred reactants are the alkenylsuccinic anhydrides in which the alkenyl radical has from about 12 to 24 carbon atoms, preferably 12 carbon atoms.

Examples of suitable hydrocarbon substituted succinic anhydrides include dipropenylsuccinic anhydride, tripropenylsuccinic anhydride, deodecenylsuccinic anhydride, tetrapropenylsuccinic anhydride, pentapropenylsuccinic anhydride and hexadecenylsuccinic anhydride.

The aminotriazole reactant is represented by the following formula:

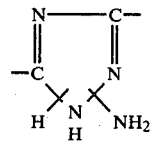

It will be understood that the hydrogen and the amino radicals are attached at the unsatisfied carbon atom bonds and that they can be interchanged in these positions.

Suitable aminotriazoles include 3-amino-1,2,4-triazole and 5-amino-1,2,4-triazole.

The hydrocarbon-substituted succinic anhydride and the aminotriazole are reacted in the proportion of from about 0.75 to 1.25 moles of said aminotriazole per mole of said hydrocarbon-substituted succinic anhydride. It is preferred, however, to prepare the reaction product by reacting approximately equimolar amounts of the hydrocarbon-substituted succinic anhydride and the aminotriazole. Effective rust inhibitors will result when the reactants are reacted within the broad proportions prescribed. However, the most effective rust inhibitor results when essentially equal mole proportions of the reactants are employed.

The reaction is facilitated by the use of a solvent for the reactants which is inert to the reactants and to the reaction product. A broad range of inert organic aromatic and aliphatic solvents are suitable for this purpose including benzene, toluene, pentane, hexane, and heptane.

This reaction is broadly conducted at a temperature ranging from about room temperature up to about 150° C. with the preferred reaction temperature being from about 50° to 100° C. In practice, it is convenient to conduct the reaction at about the reflux temperature of the solvent which has been selected for the reaction.

The following examples illustrate the preparation of the reaction product of the invention.

EXAMPLE I 100 grams (1 mole) of tetrapropenylsuccinic anhydride and 100 grams (1 mole) of 3-aminotriazole are dissolved in 1200 milliliters of xylene. The reaction mixture was refluxed for about 6 hours followed by the removal of the solvent by distillation.

The reaction product recovered contained 15.7% nitrogen. Infrared spectroscopy indicated that the product was a mixture of the tetrapropenylsuccinamide of 3-aminotriazole and the alkenylsuccinimide of 3-aminotriazole.

EXAMPLE II 142 grams (1 mole) of pentapropenylsuccinic anhydride and 100 grams (1 mole) of 3-aminotriazole are dissolved in 1200 milliliters of xylene and refluxed for about 6 hours. The solvent is removed by distillation. The product is a mixture of the pentapropenylsuccinamide acid of 3-aminotriazole and the pentapropenylsuccinimide of 3-aminotriazole.

The reaction product is employed in a motor fuel composition in a concentration ranging from about 0.005 to 0.2 weight percent. The base fuel employed for preparing a motor fuel composition according to the invention comprises a mixture of hydrocarbons boiling in the gasoline boiling range. This base fuel may consist of straight or branched chain paraffins, cycloparaffins, olefins and aromatic hydrocarbons or any mixture of these. The base fuel can be derived from straight run naphtha, polymer gasoline, natural gasoline or from catalytically cracked or thermally cracked hydrocarbons and catalytically reformed stocks. The composition or hydrocarbon component of the base fuel is not critical nor does the octane level of the base fuel have any material effect on the invention. In general, the base fuel will boil in a range from about 85° F. to about 450° F.

The fuel composition can contain any of the additives conventionally employed in gasoline. Thus, the fuel composition can contain an anti-knock compound such as a tetraalkyl lead compound including tetraethyl-lead, tetramethyl-lead and mixtures thereof. The fuel composition can also contain anti-icing additives, detergents upper cylinder lubricants and the like.

The prescribed reaction product of the invention was tested for its corrosion inhibiting properties in gasoline in the Colonial Pipeline Rust Test described below.

COLONIAL PIPELINE RUST TEST

A steel spindle, 3 and 3/16 inches long and ½ inch wide made from ASTM D-665-60 steel polished with Crystal Bay fine emergy paper is used in the Colonial Pipeline Rust Test. The spindle is placed in a 400 cc beaker with 300 cc of fuel sample which is maintained at 100° F. for ½ hour. Then 30 cc of distilled water is added. The beaker and contents are kept at 100° F. for 3½ hours. The spindle thereafter visually inspected and the percentage of rusted surface area is estimated.

The base fuel employed in the following examples was an unleaded grade gasoline having a research octane number of about 91. This gasoline consisted of about 24% aromatic hydrocarbons, 8% olefinic hydrocarbons and 68% paraffinic hydrocarbons and boiled in a range from about 90° F. to 375° F. A Base Blend was prepared from the foregoing base fuel and conventional anti-oxidant and metal deactivator in the amount of 4.5 PTB (pounds of additive per thousand barrels of the fuel composition). The results are set forth in the following Table.

TABLE

| COLONIAL PIPELINE RUST TEST | | |
|---|---|---|
| Run | Additive alone | % Rust |
| 1. | Base Blend | 50–100 |
| 2. | Base Blend + 10 PTB Example 1 | Trace, Trace |
| 3. | Base Blend + 5 PTB Example 1 | Rust Free, Trace |
| 4. | Base Blend + 1 PTB Example 1 | Rust Free, Trace |

The foregoing tests show that there was a dramatic improvement in the rust inhibiting properties of a motor fuel composition containing a range of concentrations of the novel rust inhibiting additive.

The rust inhibitor of the invention is useful in natural and synthetic oils as well as fuel compositions. It is effective in hydrocarbon mineral oils derived from petroleum including paraffin base, naphthene base or mixed paraffin-naphthene base distillate or residual oils. It is also effective in synthetic oils including polyester base and polyalkylene ether base synthetic oils. In general, the rust inhibitor is effective in concentrations ranging from about 0.001 to 5 weight percent of the oil composition. Concentrates of the rust inhibitor in an oil composition for convenience in blending the final product are also contemplated. Such a concentration may contain from about 0.001 to 50 weight percent of the additive in the oil composition.

We claim:

1. A motor fuel composition comprising a mixture of hydrocarbons in the gasoline boiling range containing a minor rust inhibiting amount of the reaction product of a hydrocarbylsuccinic anhydride and an aminotriazole, said reaction product being obtained by reacting from 0.75 to 1.5 moles of said aminotriazole per mole of said hydrocarbylsuccinic anhydride at a temperature in the range from about 20° to 150° C., said hydrocarbyl succinic anhydride being represented by the formula:

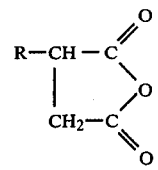

in which R is a monovalent aliphatic hydrocarbon radical having from about 6 to 30 carbon atoms and said amino triazole is represented by the formula:

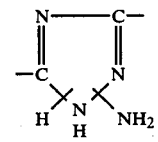

2. A motor fuel composition according to claim 1 in which said hydrocarbylsuccinic anhydride is an alkenylsuccinic anhydride in which the alkenyl radical has from 12 to 24 carbon atoms.

3. A motor fuel composition according to claim 1 in which said hydrocarbylsuccinic anhydride is tetrapropenyl succinic anhydride.

4. A motor fuel composition according to claim 1 in which said aminotriazole is 3-amino-1,2,4-triazole.

5. A motor fuel composition according to claim 1 in which said reaction product is obtained by reacting approximately equimolar amounts of said reactants.

6. A motor fuel composition according to claim 1 in which said mixture of hydrocarbons boils in the range from about 85° to 450° F.

7. A motor fuel composition according to claim 1 containing from about 0.005 to 0.2 weight percent of said reaction product.

8. A novel composition comprising the reaction product of a hydrocarbylsuccinic anhydride and an aminotriazole, said reaction product being obtained by reacting from 0.75 to 1.5 moles of said aminotriazole per mole of said hydrocarbylsuccinic anhydride at a temperature in the range from about 20° to 150° C., said hydrocarbyl succinic anhydride being represented by the formula:

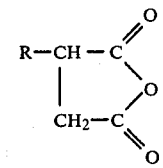

in which R is a monovalent aliphatic hydrocarbon radical having from about 6 to 30 carbon atoms and said aminotriazole is represented by the formula:

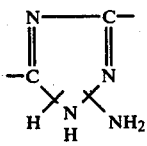

9. A composition according to claim 8 in which said hydrocarbylsuccinic anhydride is an alkenylsuccinic anhydride in which the alkenyl radical has from 12 to 24 carbon atoms.

10. A composition according to claim 8 in which said hydrocarbylsuccinic anhydride is tetrapropenyl succinic anhydride.

11. A composition according to claim 8 in which said aminotriazole is 3-amino-1,2,4-triazole.

12. A composition according to claim 8 obtained by reacting approximately equimolar amounts of said reactants.

13. An oil concentrate containing from about 0.001 to 50 weight percent of the composition of claim 8.

14. A motor fuel composition according to claim 1 in which said reaction product has a succinimide functional group.

15. A composition according to claim 8 in which said reaction product has a succinimide functional group.

* * * * *